United States Patent
Werner et al.

(10) Patent No.: US 10,430,613 B2
(45) Date of Patent: Oct. 1, 2019

(54) BLOOD GLUCOSE MEASURING DEVICE WITH RELIABLE TRANSMISSION OF VALUES TO AN EXTERNAL DEVICE

(71) Applicants: Karl Werner, Heidelberg (DE); Ulrich Porsch, Weinheim (DE); Stefan Riebel, Mannheim (DE)

(72) Inventors: Karl Werner, Heidelberg (DE); Ulrich Porsch, Weinheim (DE); Stefan Riebel, Mannheim (DE)

(73) Assignee: Roche Diabetes Care, Inc., Indianapolis, IN (US)

( * ) Notice: Subject to any disclaimer, the term of this patent is extended or adjusted under 35 U.S.C. 154(b) by 394 days.

(21) Appl. No.: 14/016,878

(22) Filed: Sep. 3, 2013

(65) Prior Publication Data

US 2014/0005951 A1 Jan. 2, 2014

Related U.S. Application Data

(63) Continuation of application No. PCT/EP2012/055215, filed on Mar. 23, 2012.

(30) Foreign Application Priority Data

Mar. 24, 2011 (EP) .................... 11159626

(51) Int. Cl.
G01N 33/48 (2006.01)
G06F 21/64 (2013.01)
G06F 19/00 (2018.01)
G06F 21/51 (2013.01)
G16H 40/63 (2018.01)
G16H 10/40 (2018.01)

(52) U.S. Cl.
CPC .......... *G06F 21/64* (2013.01); *G06F 19/3418* (2013.01); *G06F 21/51* (2013.01); *G16H 10/40* (2018.01); *G16H 40/63* (2018.01)

(58) Field of Classification Search
None
See application file for complete search history.

(56) References Cited

U.S. PATENT DOCUMENTS

| | | |
|---|---|---|
| 6,248,065 B1 | 6/2001 | Brown |
| 7,103,578 B2 | 9/2006 | Beck et al. |
| 2001/0041920 A1 | 11/2001 | Starkweather et al. |
| 2005/0203582 A1 | 9/2005 | Healy et al. |
| 2006/0101310 A1 | 5/2006 | Diamant et al. |
| 2008/0256075 A1 | 10/2008 | Claus et al. |

*Primary Examiner* — Larry D Riggs, II

(57) ABSTRACT

A blood glucose measuring device and method for transmitting measured bG values to an external device such as a computer with improved data integrity for greater reliability is disclosed. The measuring device comprises a measuring means for determining measured blood glucose values, a measured value memory in which the measured blood glucose values are stored, a data interface that is configured for a data exchange with an external data reading apparatus, and a data file system which comprises a data reading application which can be accessed by the external data reading apparatus in order to read the stored measured blood glucose values, wherein the data system file further comprises a test application that is configured to execute an integrity test for the data reading application by forming a current digital signature for the data reading application and comparing this with a digital test signature provided in the data file system.

10 Claims, 1 Drawing Sheet

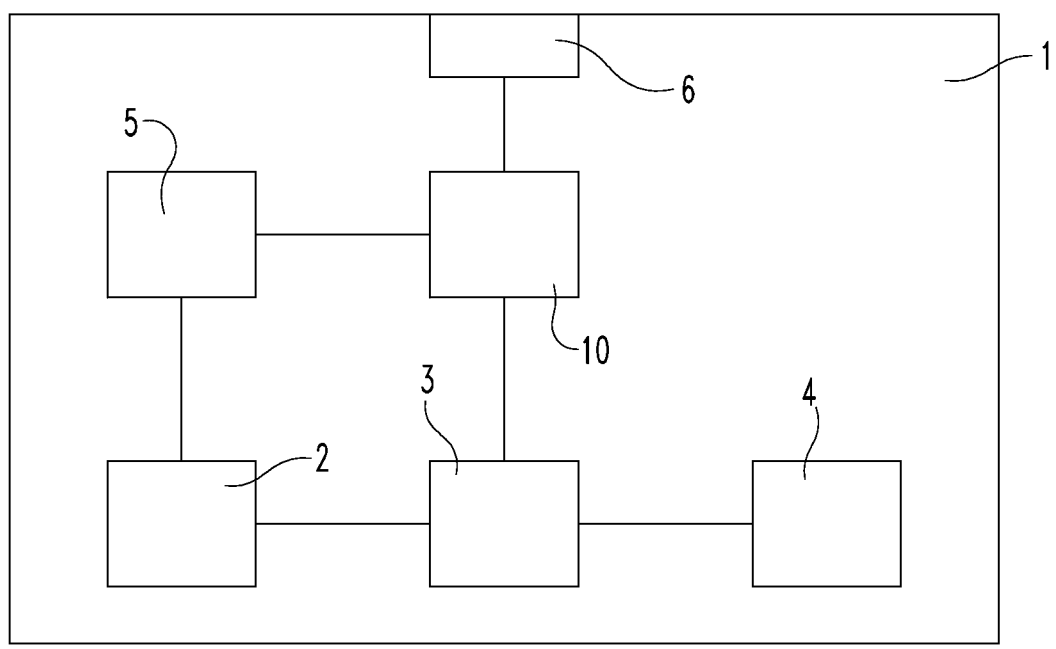

BLOOD GLUCOSE MEASURING DEVICE WITH RELIABLE TRANSMISSION OF VALUES TO AN EXTERNAL DEVICE

REFERENCE

This application is a continuation of PCT/EP2012/055215 filed Mar. 23, 2012 which is based on and claims priority to European Patent Application No. EP 11159626.8 filed Mar. 24, 2011, which are hereby incorporated by reference.

FIELD

This disclosure relates to a blood glucose measuring device, such as a blood glucose meter, using an improved method of verifying data integrity for improved reliability in transmitting measured blood glucose values to an external device such as a computer.

BACKGROUND

Blood glucose measuring devices are used in order to determine measured values for the blood glucose value. The measured blood glucose values determined in this case are stored in the form of electronic data in a memory means of the blood glucose measuring device. They are thus available for any subsequent evaluations of the measurement results. Such an evaluation can take place on the blood glucose measuring device itself and/or outside the measuring device by reading the measured blood glucose values with the aid of an external data reading apparatus via a data interface of the blood glucose measuring device. The reading apparatus is, for example, a personal computer on which software applications can be implemented in order to present the measured blood glucose values in graph form for example or to carry out any other evaluation.

In conjunction with the reading or downloading of the measured blood glucose values, it has been proposed for the measured blood glucose values which are to be read to be accessed with the aid of a browser implemented on the personal computer, as can also be used for example for access to websites. The use of a browser makes it possible to read the measured blood glucose values without providing the personal computer with specific reading software. The measured blood glucose values can be read or downloaded with the aid of a conventional browser. To read the measured blood glucose values, an application associated with the reading process is in this case started in the blood glucose measuring device itself by the browser. Within the scope of this application, the measured values are then transmitted from the blood glucose measuring device to the reading device.

Since, in this case, the reading apparatus is not equipped with special software for reading or downloading the measured blood glucose values, there is the risk that problems or faults will occur with regard to the data transmission of the measured blood glucose values, for example due to incorrect compatibility of data formats. This may lead for example to a falsification of the presentation of the measured values presented in graph form, whereby there is the risk of an incorrect diagnosis.

A monitoring system comprising a central server means is known from document U.S. Pat. No. 6,248,065 B1. The server means is coupled on the one hand to a computer system having a display means and on the other hand via a telephone network to a plurality of remote devices. In one embodiment, one of the remote devices is connected via a cable connection to a measuring device, wherein this measuring device is a blood glucose measuring device for example. The known monitoring system can be used to collect individual patient data, for example measured blood glucose values, in the central server and to thus monitor said data. In this process, measured values for the patient are initially determined with the aid of the measuring device. In order to retrieve these measured values on the remote device connected to the measuring device via the cable connection, a microprocessor in the remote device executes a collection command that is defined in what is known as a script program. In this way, the measured data are initially transmitted from the measuring device to the remote device via the cable connection. This occurs with the aid of a collection command, which is part of a script program in the remote device. For operation of the remote device, a plurality of software objects are provided that are stored in a memory of the remote device. With the aid of the script programs, operating functions are executed by the processor of the remote device, for example the retrieval of the measured values from the measuring device. The software objects stored in the memory of the remote device also comprise a script program, which verifies the integrity of script programs in the EEPROM of the remote device and, in the event of faults, activates a back-up script program in the EPROM. This is achieved by copying the back-up script program from the EPROM into the EEPROM. In this case, the script length is then also recalculated and a checksum for the script application copied into the EEPROM is calculated.

In the known system, if the measurement data, for example measured blood glucose values, collected in the remote device are now to be transmitted to the central server, a script generator, which is in turn formed in the central server, generates a script program for this purpose. The script program generated in the central server is then transmitted to the remote device, where the measured data were previously collected. When executing the script program thus received from the central server, the remote device now transmits the measurement data previously received by the measuring device to the central server. There, these data are received and stored.

SUMMARY

A blood glucose measuring device and also a method for reading measured blood glucose values from a blood glucose measuring device are provided with which the reliability for correct data transmission of the measured blood glucose values to external data reading apparatus is improved.

An embodiment of the invention comprises the concept of a blood glucose measuring device comprising a measuring means for determining measured blood glucose values, a measured value memory in which measured blood glucose values are stored, a data interface that is configured for a data exchange with an external data reading apparatus, and a data file system which comprises a data reading application accessed by the external data reading apparatus in order to read the stored measured blood glucose values, wherein the data file system further comprises a test application that is configured to execute an integrity test for the data reading application by forming a current digital signature for the data reading application and comparing this with a digital test signature provided in the data file system.

In accordance with a further aspect, a method for reading measured blood glucose values from a blood glucose measuring device is created, wherein the method comprises the following steps:

executing a test application formed in a data file system of the blood glucose measuring device, in which an integrity test is executed for a data reading application, likewise formed in the data file system, in such a way that a current digital signature is formed for the data reading application and is compared with a digital test signature provided in the data file system, and preventing a transmission of measured blood glucose values from the blood glucose measuring device to the external data reading apparatus within the scope of the data reading application and/or preventing a display of transmitted measured blood glucose values on an external display means if the test application reveals that the current digital signature and the digital test signature inadmissibly fail to match.

With the aid of invention embodiments, it is ensured that the execution of a data reading application is implemented with use of a correct and intact version of the data reading application. Before it is possible to start the actual download of measured blood glucose values from the blood glucose measuring device to the external reading apparatus, which is a personal computer for example, an integrity or reliability test is carried out for the data reading application. In this case, a current digital signature is formed for the data reading application and is compared with a digital test signature which is stored in the blood glucose measuring device and which can be accessed by the test application in the data file system.

In one embodiment, the access to the measured blood glucose values for downloading purposes is then only released if the integrity test reveals that the data reading application is intact. Otherwise, the access to the measured blood glucose values, that is to say an actual further execution of the data reading application in the form of the download of the measured blood glucose values, may be blocked.

In accordance with a further embodiment, the execution of the data reading application may not only cause the (mere) download or retrieval of the measured blood glucose values, but, in addition, a presentation of the downloaded measured blood glucose values, that is to say a display on an electronic display means that is comprised by the external data reading apparatus or is coupled thereto. The display can be executed within the scope of a display application that is part of the data reading application or is formed separately therefrom, for example as a sub-application, wherein it can then in particular be retrieved preferably automatically by the data reading application. The display can take place at the same time as the download and/or in a chronologically delayed manner relative thereto. In accordance with this embodiment, the access to the measured blood glucose values for actual retrieval within the scope of the data reading application may then likewise be blocked. Alternatively, a download of the measured values, in particular in the form of raw data that are yet to be processed for illustration in graph form, may still be possible even if there is a lack of integrity of the data reading application, however the subsequent display of the downloaded data is inhibited. For example, potentially erroneously downloaded measured blood glucose values are thus prevented from being displayed, for example.

The current digital signature is formed for the software or program code of the data reading application itself provided on the blood glucose measuring device. This is thus an integrity test for the software or program code of the data reading application and is performed on the data, in particular the measured blood glucose values. In one embodiment, this preferably occurs by means of a client device, for example a browser, running on the external data reading apparatus, during operation of which the data reading application in the blood glucose measuring device is accessed in order to read data in order to execute said data reading application within the scope of the operation of the client device. The data reading application is then in this regard a client-executable application.

The test application may (only) be started automatically in the event of access of the external data reading apparatus to the data reading application. In this embodiment, the test application is configured, in a manner triggered by the access of the external data reading apparatus to the data reading application, to execute an integrity test for the data reading application by forming the current digital signature for the data reading application and comparing it with the digital test signature provided in the data file system. Alternatively or additionally, an integrity test for the data reading application can be carried out proactively, either once or a number of times, for example when the blood glucose measuring device is switched on or triggered by another event, such as a firmware change, without access to the data reading application actually being given at this moment in time by the external data reading apparatus. In accordance with the embodiments described above, a current digital signature is provided in each case for comparison with the digital test signature. The term "current" within the context of the meaning used here indicates that it is the digital signature for the present version of the data reading application at the moment at which the test application is executed, wherein this signature may be present in correct or incorrect form, wherein the latter case then leads to the above-described consequences.

The external data reading apparatus accesses the data reading application, for example by means of a browser means implemented on the external reading apparatus. In this case, this is an application on the external data reading apparatus that is not normally prepared specifically for the method for reading and for selectively displaying the measured blood glucose values. Rather, the browser means can be used in a versatile manner in various applications, for example in the event of access to websites. The browser means accesses the data reading application in the data file system of the blood glucose measuring device in order to start a data reading process and a selectively subsequent presentation of the measured values. Only if the test application reveals that the data reading application is still present in correct form can a download and a display, which may or may not be provided, of the measured blood glucose values then actually take place. A correct and reliable transmission of the measured blood glucose values from the blood glucose measuring device to the external data reading apparatus is thus assisted. The data transmission itself can be executed selectively with further security mechanisms, for example with use of an encryption of the measured values to be transmitted.

The digital signature is used for the integrity test of the data reading application. This is a cryptographic method, in which a number value is calculated for the software or program code of the data reading application. Digital signature methods are known per se in various embodiments. For example, these include what is known as RSA or DSA. The signature is often calculated with inclusion of what is known as a hash value. A simple form of the digital signature check in the meaning used here is what is known as a checksum test.

Certain embodiments of the invention have a non-volatile signature memory, in which the digital test signature is stored. The non-volatile signature memory is designed for example as an electrically erasable programmable memory (EEPROM).

An expedient embodiment of the invention can be characterised by a firmware module, which is configured to read the digital test signature from the non-volatile signature memory and to forward it to the data file system. The digital test signature can be provided in the data file system before an external reading apparatus actually accesses the data reading application. In this regard, the blood glucose measuring device is then already proactively set up for such an access. However, the digital test signature may also be transmitted from the signature memory into the data file system in real time when access of the external data reading apparatus is determined. In an embodiment, an up-to-dateness test for the digital test signature stored in the data file system can also be executed in this manner. If access to the data reading application is thus determined, the digital test signature currently read from the signature memory is compared with a digital test signature provided already in the data file system in a step for the up-to-dateness test. Such an up-to-dateness test may also be carried out in a manner detached from an actual access to the data reading application and repeatedly, for example at predefined intervals.

In accordance with an embodiment of the invention, the test application is formed as a sub-application of the data reading application, in such a way that the sub-application is started by the data reading application once this has been started itself. In this embodiment, the data reading application calls up the test application itself. In an alternative embodiment, in the event of a determined attempt to access the data reading application, the test application is first called up and run before the data reading application itself is actually started.

In certain embodiments of the invention, the data reading application and the test application are each formed as a script application. For example, the applications can be formed as JavaScript applications. Script applications can be called up and started arbitrarily by a browser means implemented on the external data reading apparatus.

In accordance with an embodiment of the invention, the digital test signature in the data file system can be provided in a configuration file. In this embodiment, the digital test signature is integrated into a configuration file that may selectively comprise further electronic data that in particular determine parameters for the operation of the blood glucose measuring device. Such operating parameters include for example the measurement unit in which the measured blood glucose values are displayed and the language that is used in the displayed graphs.

In certain embodiments of the invention, the data reading application can be configured to execute a measured value integrity test for individual measured blood glucose values and/or a group of measured blood glucose values by forming a digital measured value signature and comparing this with a digital measured value test signature. In this embodiment, the security mechanisms provided for the data transmission are supplemented when reading the measured blood glucose values by an integrity test for the measured values themselves. The digital measured value test signature can also be stored in the signature memory. The digital measured value test signature can be handled in various embodiments in accordance with the above explanations for the digital test signature. Intentional or unintentional measured value falsifications can thus be eliminated.

In certain embodiments of the invention, the data reading application and/or the test application is/are configured to prevent a download of the measured blood glucose values to the data reading apparatus and/or a display of downloaded measured blood glucose values if the test application reveals that the current digital signature and the digital test signature inadmissibly fail to match. In particular, there is then no match if the two signatures do not have the same value.

In one embodiment, the method may comprise the following steps:

accessing an external data reading apparatus via a data interface to a data reading application in a data file system of a blood glucose measuring device, executing a test application formed in the data file system of the blood glucose measuring device, in which an integrity test is executed for the data reading application in such a way that a current digital signature is formed for the data reading application and is compared with a digital test signature provided in the data file system, releasing the execution of the data reading application if, during the test application, it is determined that the current digital signature for the data reading application corresponds to the digital test signature, and transmitting measured blood glucose values from the blood glucose measuring device to the external data reading apparatus within the scope of the data reading application.

BRIEF DESCRIPTION OF THE DRAWING

FIG. 1 shows a schematic illustration of a system for determining and evaluating measured blood glucose values.

DETAILED DESCRIPTION

The invention will be explained in greater detail hereinafter on the basis of exemplary embodiments with reference to FIG. 1.

FIG. 1 shows a schematic illustration of a system for determining and evaluating measured blood glucose values. The system comprises a blood glucose measuring device 1, which, with the aid of a blood glucose measuring means 2, is configured to determine measured blood glucose values for blood samples, whether in a continuous and/or discontinuous operating mode. Blood glucose measuring means are known per se in various embodiments and therefore will not be explained in greater detail here.

A firmware module 3 comprises embedded software codes in associated memory elements. In accordance with the common understanding, these codes are components not determined by application software and linked in terms of function to the hardware of the blood glucose measuring device 1. The software code contained in the firmware module 3 cannot be influenced by the user, that is to say in particular a patient or medical employee.

The firmware module 3 is configured to access a signature memory 4 in the blood glucose measuring device 1. The signature memory 4 is a non-volatile memory, for example an EEPROM, in which digital signatures are stored.

The measured blood glucose values determined with the aid of the blood glucose measuring means 2 are stored in a measured value memory 5. This is preferably achieved by means of what are known as embedded reports. The information stored in the measured value memory 5 concerning measured blood glucose values can be downloaded or read with the aid of external data reading apparatus 7 via a data interface 6 of the blood glucose measuring device 1. The external data reading apparatus 7 is, for example, a personal computer. The data is transmitted between the data interface 6 of the blood glucose measuring device 1 and a data interface 8 comprised by the external data reading apparatus 7 via a wired or wireless communication connection, selectively with inclusion of the Internet and/or other data communication networks.

On the external data reading apparatus 7, a client device formed here as a browser means 9 is implemented, by means of which a data file system 10 in the blood glucose measuring device 1 can be accessed via the data interfaces 6, 8. The data file system 10 comprises various electronic data and pieces of information. These include, in particular, executable software applications which for example are present as script applications, preferably as JavaScript applications. Measured values provided for the reading or download processes can also be stored in the data file system 10, however. In addition, one or more digital test signatures are provided in the data file system 10 and have preferably been transmitted from the signature memory 4 into the data file system 10 by means of the firmware module 3.

If, in the described system, measured blood glucose values are now to be downloaded from the blood glucose measuring device 1 to the external data reading apparatus 7, the browser means 9 accesses a data reading application in the data file system 10 via the data interfaces 6, 8. This is preferably achieved in that a script application provided on the external data reading apparatus 7 is executed on the external data reading apparatus 7 by means of the browser means 9, which forms a client running on the data reading apparatus 7, and provides a step for access to the data reading application in the blood glucose measuring device 1 in such a way that the data reading application is then executed in the browser means 9 within the scope of the operation thereof. The data reading application is thus arranged in this case in the blood glucose measuring device 1, specifically as a client- or browser-executable application, and is executed on data of the data file system 10 by means of the browser means 9. Examples of browser-executable applications include what are known as flash animations or Java applets, inter alia.

If such an access to the data reading application is determined in the blood glucose measuring device 1, a further application provided in the data file system 10 is started, specifically a test application. Within the scope of the executed test application, an integrity test is carried out for the software code forming the data reading application, wherein a current digital signature is established for the software code and is compared with a digital test signature associated with the data reading application. If a match between the digital signatures is determined, the measured blood glucose values can then be downloaded or read by means of execution of the data reading application. Otherwise, an execution or further execution of the data reading application, for example if first initial steps have already begun without actual data reading, is blocked.

The digital test signature for the data reading application consulted for the test application was previously stored in the signature memory 4. The digital test signature may already be stored proactively in the data file system 10 before an access to the data reading application. A real-time access to the digital test signature when determining (attempted) access to the data reading application by the browser means 9 can also be provided, however. The digital test signature can be integrated into a configuration file in the data file system 10.

In an alternative embodiment, the integrity test for the data reading application may be carried out independently of an actual access of the external data reading apparatus 7 in the blood glucose measuring device 1, for example when the device is started.

The stored digital test signature is brought to the current state by means of the firmware module 3 when, for example, a new version of the data reading application is installed. Otherwise, the provided separation of signature memory 4 on the one hand and firmware module 3 on the other hand enables an updating or an exchange of the firmware without affecting the storage of the digital test signature(s). The data reading application can also be updated or amended independently of the firmware. The digital test signature stored in the signature memory 4 is also updated subsequently thereto, such that the correct test signature is stored for future integrity tests.

Thus, embodiments of the blood glucose measuring device with reliable transmission of values to an external device are disclosed. One skilled in the art will appreciate that the teachings can be practiced with embodiments other than those disclosed. The disclosed embodiments are presented for purposes of illustration and not limitation, and the invention is only limited by the claims that follow.

What is claimed is:

1. A blood glucose measuring device, comprising:
   a measuring means for determining measured blood glucose values,
   a measured value memory in which the measured blood glucose values are stored,
   a data interface that is configured for a data exchange with an external data reading apparatus, and
   a data file system which comprises a data reading application that is executed by means of an external data reading apparatus and that is configured to provide the stored measured blood glucose values for reading by means of the external data reading apparatus,
   wherein the data system file further comprises a test application that is configured to execute an integrity test for the data reading application by forming a current digital signature for the data reading application and comparing this with a digital test signature provided in the data file system and;
   wherein the data reading application is configured to
   download of the measured blood glucose values to the external data reading apparatus, and
   prevent a display of downloaded measured blood glucose values if the test application reveals that the current digital signature and the digital test signature inadmissibly fail to match.

2. The blood glucose measuring device according to claim 1, further comprising a non-volatile signature memory, in which the digital test signature is stored.

3. The blood glucose measuring device according to claim 2, further comprising a firmware module, which is configured to read the digital test signature from the non-volatile signature memory and to forward it to the data file system.

4. The blood glucose measuring device according to claim 1, wherein the test application is formed as a sub-application of the data reading application in such a way that the sub-application is started by the data reading application once this has been started itself.

5. The blood glucose measuring device according to claim 1, wherein the data reading application and the test application are each formed as a script application.

6. The blood glucose measuring device according to claim 1, wherein the digital test signature is provided in the data file system in a configuration file.

7. The blood glucose measuring device according to claim 1, wherein the data reading application is configured to execute a measured value integrity test for individual measured blood glucose values and/or a group of measured blood glucose values by forming a digital measured value signature and comparing this with a digital measured value test signature.

8. A method for reading measured blood glucose values from a blood glucose measuring device, comprising:
executing a test application formed in a data file system of the blood glucose measuring device, by means of which an integrity test is executed for a data reading application, likewise formed in the data file system, in such a way that a current digital signature is formed for the data reading application and is compared with a digital test signature provided in the data file system, and
preventing a transmission of measured blood glucose values from the blood glucose measuring device to the external data reading apparatus, which executes the data reading application, within the scope of the data reading application and/or a display of transmitted measured blood glucose values on an external display means if the test application reveals that the current digital signature and the digital test signature inadmissibly fail to match.

9. A blood glucose measuring device, comprising:
a measuring means for determining measured blood glucose values,
a measured value memory in which the measured blood glucose values are stored,
a data interface that is configured for a data exchange with an external data reading apparatus, and
a data file system which comprises a data reading application that is executed by means of an external data reading apparatus and that is configured to provide the stored measured blood glucose values for reading by means of the external data reading apparatus,
wherein the data system file further comprises a test application that is configured to execute an integrity test for the data reading application by forming a current digital signature for the data reading application and comparing this with a digital test signature provided in the data file system and;
wherein the data reading application is configured to
download of the measured blood glucose values to the external data reading apparatus if the test application reveals that the current digital signature and the digital test signature match, and
prevent a download of the measured blood glucose values to the external data reading apparatus if the test application reveals that the current digital signature and the digital test signature inadmissibly fail to match.

10. A blood glucose measuring device, comprising:
a measuring means for determining measured blood glucose values,
a measured value memory in which the measured blood glucose values are stored,
a data interface that is configured for a data exchange with an external data reading apparatus, and
a data file system which comprises a data reading application that is executed by means of an external data reading apparatus and that is configured to provide the stored measured blood glucose values for reading by means of the external data reading apparatus,
wherein the data system file further comprises a test application that is configured to execute an integrity test for the data reading application by forming a current digital signature for the data reading application and comparing this with a digital test signature provided in the data file system and;
wherein the test application is configured to
download of the measured blood glucose values to the external data reading apparatus if the test application reveals that the current digital signature and the digital test signature match, and
prevent a download of the measured blood glucose values to the external data reading apparatus if the test application reveals that the current digital signature and the digital test signature inadmissibly fail to match.

* * * * *